US012746200B2

(12) United States Patent
Kan et al.

(10) Patent No.: US 12,746,200 B2
(45) Date of Patent: *Sep. 29, 2026

(54) PHARMACEUTICAL COMPOSITION FOR CONTROLLED RELEASE OF WEAK ACID DRUGS AND USES THEREOF

(71) Applicant: Pharmosa Biopharm Inc., Taipei City (TW)

(72) Inventors: Pei Kan, Taipei City (TW); Yi Fong Lin, New Taipei City (TW); Ko Chieh Chen, Taipei City (TW)

(73) Assignee: Pharmosa Biopharm Inc., Taipei City (TW)

( * ) Notice: Subject to any disclaimer, the term of this patent is extended or adjusted under 35 U.S.C. 154(b) by 0 days.

This patent is subject to a terminal disclaimer.

(21) Appl. No.: 19/179,554

(22) Filed: Apr. 15, 2025

(65) Prior Publication Data

US 2025/0241856 A1 Jul. 31, 2025

Related U.S. Application Data

(63) Continuation of application No. 16/568,801, filed on Sep. 12, 2019, now abandoned.

(60) Provisional application No. 62/731,101, filed on Sep. 14, 2018.

(51) Int. Cl.

| | |
|---|---|
| ***A61K 9/127*** | (2025.01) |
| ***A61K 31/191*** | (2006.01) |
| ***A61K 31/505*** | (2006.01) |
| ***A61K 47/12*** | (2006.01) |
| ***A61K 47/28*** | (2006.01) |
| ***A61K 47/40*** | (2006.01) |

(52) U.S. Cl.

CPC ............ *A61K 9/127* (2013.01); *A61K 31/191* (2013.01); *A61K 31/505* (2013.01); *A61K 47/12* (2013.01); *A61K 47/28* (2013.01); *A61K 47/40* (2013.01)

(58) Field of Classification Search

None

See application file for complete search history.

(56) References Cited

U.S. PATENT DOCUMENTS 5,262,168 A 11/1993 Lenk et al.
5,616,341 A 4/1997 Mayer et al.
5,759,573 A 6/1998 Kim
5,939,096 A * 8/1999 Clerc .................. A61K 9/1278 424/450
2003/0124181 A1 7/2003 Tardi et al.
2004/0247628 A1 12/2004 Lintz et al.
2008/0058294 A1 3/2008 Barenholz et al.
2010/0183721 A1* 7/2010 Williams ............. A61K 9/1694 977/788
2011/0136818 A1 6/2011 Clozel
2012/0128757 A1* 5/2012 Kikuchi ............... A61K 9/1278 514/254.1
2013/0072490 A1 3/2013 Clark et al.
2013/0216606 A1* 8/2013 Venkatraman ......... A61K 9/127 514/530
2014/0005239 A1 1/2014 Cook et al.
2015/0174070 A1 6/2015 Cheng et al.
2016/0058705 A1 3/2016 Rajadas et al.
2020/0085741 A1 3/2020 Kan et al.
2021/0113464 A1 4/2021 Sawa et al.
2021/0369752 A1 12/2021 Perkins et al.

FOREIGN PATENT DOCUMENTS

CN 101278913 A 4/2008
CN 103260702 B 8/2021
JP H08509230 A 10/1996
JP 2010018632 A 1/2010
JP 2015524391 A 8/2015
RU 2279292 C2 7/2006
RU 2657510 C2 6/2018
WO WO-9625147 A1 * 8/1996 ........... A61K 9/1278
WO 2012058483 A1 5/2011
WO 2017135948 A1 8/2017

OTHER PUBLICATIONS

T Higenbottam et al., "Long-term intravenous prostaglandin (epoprostenol or iloprost) for treatment of severe pulmonary hypertension" Heart, Aug. 1998, pp. 151-155, vol. 80.
Wikipedia, "Prostaglandin", Jan. 10, 2018 (Jan. 10, 2018), retrieved on Oct. 31, 2019 from https://en.wikipedia.org/w/index.php?title=Prostaglandin&oldid=819650728.
International Search Report and Written Opinion for PCT/US19/50769, mailed Nov. 27, 2019.
Office action and Search Report for TW Application No. 108133035 mailed May 28, 2020.
Extended European Search Report for corresponding EP Application No. 19859476.4, mailed May 6, 2022.
Pritesh P. Jain et al., "Liposomal nanoparticles encapsulating iloprost exhibit enhanced vasodilation in pulmonary arteries," International Journal of Nanomedicine, Jul. 2014, pp. 3,249-3,261, vol. 9.
Office action for corresponding JP Application No. 2021-513875, mailed Jun. 7, 2022.
Office action for corresponding JP Application No. 2021-513875, mailed Dec. 27, 2022.
Office Action for corresponding Russia Application No. 2021106329/04(013685), dated Jan. 27, 2023.

(Continued)

*Primary Examiner* — Celeste A Roney
(74) *Attorney, Agent, or Firm* — Pilloff Passino & Cosenza LLP; Rachel K. Pilloff; Sean A. Passino

(57) ABSTRACT

Provided herein are pharmaceutical compositions containing at least one liposome, said liposome comprise an external lipid bilayer including at least one vesicle-forming phospholipid and less than 15 mole % of sterol; and an internal aqueous medium including a weak acid drug and weak acid salt. The pharmaceutical compositions reduce the burst release of the weak acid drug. Also provided is the use of the pharmaceutical composition disclosed herein to treat respiratory diseases and reduce the side effect of the weak acid drug.

16 Claims, 1 Drawing Sheet

(56) References Cited

OTHER PUBLICATIONS

D.A. Kharkevich, Pharmacology, Manual, 10th edition. M.: GEOTAR-Media, 2010, p. 73-74).
Office Action for corresponding Russia Application No. 2021106329/04(013685), dated Jun. 26, 2023.
Belikov V.G., Pharmaceutical Chemistry, Manual, M: MEDpress-Inform, 2007, pp. 27-29.
S.O. Klyuchnikov et al., Acute respiratory diseases in children, Russian Bulletin of Perinatology and Pediatrics, Annex 3.2008—Manual for physicians. I: Medkniga, 2009, see pp. 3, 9).
Zhulenko V.N et al., Pharmacology. M.: KolosS, 2008, pp. 34-35.
SIPO office action dated Sep. 15, 2023 in application No. 201980058554.8.
Liang Fang, Pharmacology, 3rd Edition, Published Mar. 2016 by China Medical Science and Technology Press China, p. 287.
Indonesian office action dated Nov. 3, 2023 in application No. P00202101793.
Aparna Saigala, Controlled Release Inhalable Polymeric Microspheres for Treatment of Pulmonary Arterial Hypertension, Current Pharmaceutical Design, 2015; 21, 5868-5876.
Hearing Notice for India Application No. 202117015922, mailed Dec. 18, 2023.
Office action for Korea Application No. 10-2021-7007375, mailed Dec. 13, 2023.
Office action for Saudi Arabia Application No. 521421347, mailed Dec. 3, 2023.
Office action dated Mar. 1, 2024 from SIPO application No. 201980058554.8.
Office action dated Jan. 22, 2024 from IMPI application No. MX/a/2021/001820.
Weiguo Jing, et al., Headgroup structure and fatty acid chain length of the acidic phospholipids modulate the interaction of membrane mimetic vesicles with the antimicrobial peptide protegrin-1, J Pept Sci. Nov. 2005;11(11):735-43. (doi: 10.1002/psc.702).
Dorota Matyszewska et al., The effect of acyl chain length and saturation on the interactions of pirarubicin with phosphatidylethanolamines in 2D model urothelial cancer cell membranes, Journal of Molecular Liquids vol. 323, Feb. 1, 2021, 114633 (doi.org/10.1016/j.molliq.2020.114633).
Office action for corresponding Korea Application No. 10-2021-7007375, mailed Apr. 22, 2024.
Office action for corresponding Saudi Arabia Application No. 521421347, mailed Jun. 30, 2024.
Office action for corresponding SIPO Application No. 201980058554.8, mailed Aug. 2, 2024.
Office action for corresponding Korea Application No. 10-2024-7024751, mailed Aug. 26, 2024.
Office action for corresponding Japan Application No. 2023-111973, mailed Oct. 21, 2024.
Piel, G. et al., Betamethasone-in-cyclodextrin-in-liposome: The effect of cyclodextrins on encapsulation effiiency and release kinetics. Inter Jour Pharm. 312, 75-82. DOI: 10.1016/j.ijpharm.2005.12.044 (Year: 2006).
Briuglia et al. (Influence of cholesterol on liposome stability and on in vitro drug release, Drug Delivery and Translational Research vol. 5, pp. 231-242) (Year: 2015).
Notice of Final Rejection dated Apr. 18, 2025 from KR application No. 10-2024-7024751.
Office Action issued in corresponding BR Application No. BR112021003256-8, mailed May 14, 2025.
OA of the corresponding JP divisional application, mailed on Aug. 5, 2025.
Office Action issued in corresponding Singapore SG Application No. 11202102518V dated Jan. 20, 2026.
Notice of Final Rejection (Original) South Korean KR Application No. 1020247024751 dated Jan. 29, 2026.

* cited by examiner

PHARMACEUTICAL COMPOSITION FOR CONTROLLED RELEASE OF WEAK ACID DRUGS AND USES THEREOF

CROSS-REFERENCE TO RELATED APPLICATIONS

This application is a continuing application of U.S. patent application Ser. No. 16/568,801, filed Sep. 12, 2019, which claims the benefit of U.S. Application No. 62/731,101 filed on Sep. 14, 2018, the entire disclosures of each of which are incorporated herein by reference.

FIELD

Disclosed herein are pharmaceutical compositions comprising at least one liposome encapsulating a weak acid drug, wherein a lower amount of sterol in the external lipid bilayer of the liposome reduces or prevents a burst release and/or sustains the release of the weak acid drug.

BACKGROUND

Liposomes are microstructures composed of a bilayer of natural or synthetic lipids, forming an interior compartment serves as a reservoir for a therapeutic agent. A variety of liposomal compositions have been designed as drug delivery vehicles with different size, permeability and stability, all of which are designed to provide sustained drug release. However, these sustained release liposomal compositions typically exhibit high initial burst of drug release, resulting in higher side effects during the burst release and/or plasma drug levels outside the therapeutic window.

The release profile of a liposomal composition depends on the structure of the liposomal membrane and affects the performance of liposomes. Therefore, control over the release profile becomes an important prerequisite for the effective use of liposomes as a drug delivery vehicle. For example, cholesterol is added to the external lipid bilayer to increase membrane rigidity, stability and decrease lipid bilayer permeability (S. Kaddah et al., *Food Chem Toxicol.* 2018 March; 113:40-48). S. Kaddah et al. shows the release of encapsulated drug decreases with the increase of the cholesterol (up to 30%) in the liposome bilayer. E. Corvera et al. (Biochim Biophys Acta. 1992 Jun. 30; 1107 (2): 261-70) teaches the addition of low concentrations of cholesterol (5-8%) into DMPC and DPPC liposomes decreases liposome stability and increases membrane permeability.

There remains a need for a liposomal composition without initial burst release to reduce potential side effect and extend the therapeutic efficacy for a weak acid drug. The present invention addresses these and other needs.

BRIEF SUMMARY OF THE INVENTION

The present invention provides a pharmaceutical composition comprising one or more liposomes suspended in an external medium, said liposome comprising: (a) an external lipid bilayer, comprising at least one vesicle-forming phospholipid and less than 15 mole % of sterol and (b) an internal aqueous medium, comprising a weak acid drug and a weak acid salt, wherein less than 65 weight % of the weak acid drug is released into the external medium within 1 hour after the administration of the pharmaceutical composition.

The present invention also discloses methods of treating a respiratory disease, comprising the step of administering the pharmaceutical composition described herein.

Also provided is a method for reducing the side effect of a weak acid drug, comprising the step of administering to a subject in need of taking the weak acid drug an effective amount of the pharmaceutical composition described herein.

The terms "invention", "the invention", "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

Illustrative embodiments of the present invention are described in detail below with reference to the following figures.

DETAILED DESCRIPTION

Figure 1:
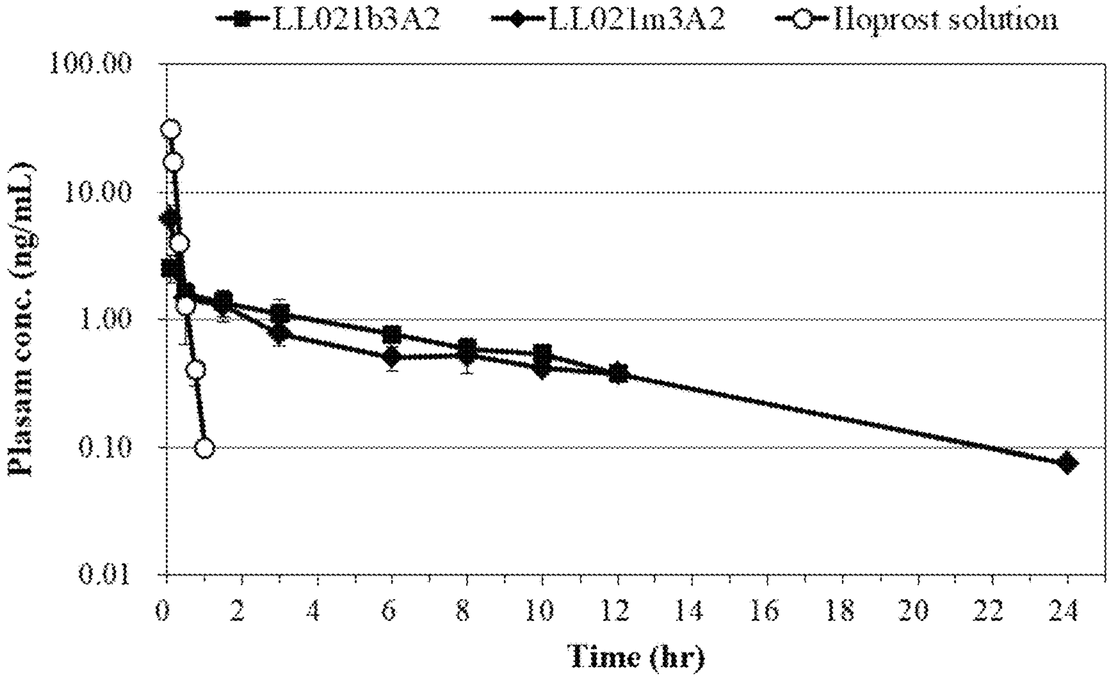
FIG. 1 is a line graph showing the log of mean plasma iloprost concentration of rats administered with a liposomal composition comprising iloprost, bicarbonate and HP-β-CD (LL021b3A2), a liposomal composition comprising iloprost, bicarbonate and RM-β-CD (LL021m3A2), or an iloprost solution.

As used herein, the articles "a" and "an" refer to one or more than one (i.e., at least one) of the grammatical object of the article. By way of example, "an element" means one element or more than one element.

All numbers are modified by the term "about". As used herein, the term "about" refers to a range of ±10% of a specified value.

The term "comprise" or "comprising" is generally used in the sense of include/including which means permitting the presence of one or more features, ingredients or components.

The term "subject" can refer to a vertebrate having a respiratory disease or to a vertebrate deemed to be in need of treatment for a respiratory disease. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The term "treating" refers to both therapeutic treatment and prophylactic or preventative measures. Those in need of treatment include those already with a respiratory disease or related disorder as well as those prone to having a respiratory disease or related disorder or those in which the respiratory disease is to be prevented.

A weak acid drug as used herein, unless indicated to the contrary or otherwise evident from the context, also include its pharmaceutically acceptable salt and its protonated form. In one embodiment, a weak acid drug contains at least one functional group selected from the group consisting of a carboxyl group (—COOH), a hydroxyl group (—OH), a phosphate group (—$PO_4$) and any combination thereof. In another embodiment, a weak acid drug has a pKa of between 1 to less than about 7, between 2 to less than about 6, between 2 to 6.9, or between 2.5 to 6. A weak acid drug may also contain one or more functional groups in addition to the above-mentioned carboxyl group (—COOH), hydroxyl group (—OH), and phosphate group (—$PO_4$); such additional functional group(s) should not significantly change the acidity of the drug from that of its non-functionalized counterparts. In an embodiment, the weak acid drug is used to treat pulmonary hypertension. In another embodiment the weak acid drug is prostaglandin, prostacyclin receptor agonist, glucocorticoid or non-steroidal anti-inflammatory drug. Table 1 shows the non-limiting examples of the weak acid drug of the present invention.

TABLE 1

Weak acid drugs suitable in the present invention

| Drug category | Drug species |
|---|---|
| Prostaglandins | Prostaglandin E1 (PGE1) |
| | Prostaglandin E2 (PGE2) e.g., dinoprostone |
| | Epoprostenol |
| | Iloprost (prostacycline analog) |
| | Beraprost (prostacycline analog) |
| | Treprostinil (prostacycline analog) |
| | Ralinepag (APD811) |
| Prostacyclin (IP) receptor agonist | MRE-269 (ACT-333679) |
| | Ambrisentan |
| | Bosentan |
| | Macitentan |
| Endothelin (ET) receptor antagonist | Hydrocortisone sodium succinate |
| Glucocorticoids (GCs) | Methylprednisolone sodium succinate |
| | Methylprednisolone Hemisuccinate (MPSS) |
| | Hydrocortisone sodium phosphate |
| | Betamethasone sodium phosphate |
| | Dexamethasone sodium phosphate |
| | Dexamethasone hemisuccinate |
| | Aspirin (acetylsalicylic acid) |
| | Salicylic acid and other salicylates |
| | Ibuprofen sodium |
| Non-steroidal anti-inflammatory drug (NSAID) | Dexibuprofen |
| | Naproxen sodium |
| | Fenoprofen |
| | Ketoprofen sodium |
| | Dexketoprofen |
| | Flurbiprofen |
| | Oxaprozin |
| | Loxoprofen |
| | Salsalate (Disalcid) |
| | Indomethacin sodium |
| | Tolmetin |
| | Etodolac |
| | Ketorolac sodium |

TABLE 1-continued

Weak acid drugs suitable in the present invention

| Drug category | Drug species |
|---|---|
| | Diclofenac sodium |
| | Aceclofenac |
| | Piroxicam |
| | Meloxicam |
| | Lornoxicam |
| | Antibiotic |
| | Cephalexin sodium |
| Others | Carbenoxolone sodium |
| | Chlorambucil sodium |
| | Warfarin |
| Anticoagulant | |

As used herein, the terms "encapsulation", "loaded" and "entrapped" can be used interchangeably, and refer to the incorporation or association of a biologically active agent (e.g., iloprost) in the internal aqueous medium of a liposome.

The present disclosure provides a pharmaceutical composition containing one or more liposomes suspended in an external medium, said liposome comprising: (a) an external lipid bilayer, comprising at least one vesicle-forming phospholipid and less than 15 mole % of sterol and (b) an internal aqueous medium, comprising a weak acid drug and a weak acid salt, wherein less than 65 weight % of the weak acid drug is released into the external medium within 1 hour after the administration of the pharmaceutical composition.

In an exemplary embodiment, the sterol in the external lipid bilayer is less than 15, 14, 13, 12, 11, 10, 9, 8, 7, 6, 5, 4, 3, 2, 1, 0.5 mole %. In another exemplary embodiment, the external lipid bilayer is substantially free of sterol.

The encapsulation efficiency of the weak acid drug in the pharmaceutical composition is above about 70%, 75% or 80%.

The pharmaceutical composition reduces the burst release of the encapsulated weak acid drug. In an embodiment, less than about 70%, 69%, 68%, 67%, 66% or 65% of the weak acid drug is released within 1 hours after the administration of the pharmaceutical composition. As a result, the side effects of the weak acid drug at the target site (for example, cough, throat irritation, pharyngeal pain, epistaxis, hemoptysis and wheezing in the upper respiratory tract) are reduced compared to that of a pharmaceutical composition wherein the sterol in the external lipid bilayer is equal to or over 15 mole %. Furthermore, the pharmaceutical composition extends the release of the weak acid drug and reduces the dosing frequency.

In one embodiment, the burst release of the weak acid drug from the disclosed pharmaceutical composition is further reduced with the addition or encapsulation of a cyclodextrin in the internal aqueous medium. Non-limiting examples of cyclodextrin include α-CD, β-CD, γ-CD, 2-Hydroxypropyl β-CD (HP-β-CD), sulfobutylether β-CD (SBE-β-CD), randomly methylated β-CD (RM-β-CD) or a combination thereof. Preferably, the cyclodextrin is HP-β-CD, RM-β-CD or a combination thereof. In one exemplary embodiment, the molar ratio of the weak acid drug to cyclodextrin (drug/CD ratio) is less than or equal to about 0.06, 0.055, 0.05, 0.045, 0.04, 0.035 or 0.03.

Also disclosed is a method for treating a respiratory disease comprising the step of administering to a subject in need thereof an effective amount of a pharmaceutical composition disclosed herein, wherein the amount of sterol in the external lipid bilayer is less than 15 mole %. The burst release of the weak acid drug of the pharmaceutical composition disclosed herein is reduced compared to that of a pharmaceutical composition with equal to or more than 15 mole % of sterol in the external lipid bilayer. Non-limiting examples of the respiratory disease include pulmonary hypertension and interstitial lung disease.

Further disclosed is the use of the pharmaceutical composition disclosed herein to treat a respiratory disease or the use of the pharmaceutical composition disclosed herein for the manufacture of a medicament for the treatment of a respiratory disease.

The present invention is also directed to methods for reducing the side effect of a weak acid drug, comprising administering to a subject in need of taking the weak acid drug an effective amount of a pharmaceutical composition disclosed herein, wherein the amount of sterol in the external lipid bilayer is less than 15 mole %.

In some embodiments, the pharmaceutical composition disclosed herein is administered by inhalation to reduce the side effect of the weak acid drug in the upper respiratory tract.

A. Liposomal Components

The term "liposome" as used herein refers to microscopic vesicles or particles made up of one or more lipid bilayers enclosing an internal aqueous medium. To form liposomes, the presence of at least one "vesicle-forming lipid" is needed, which is an amphipathic lipid capable of either forming or being incorporated into a lipid bilayer. Any suitable vesicle-forming lipid may be used to form the lipid bilayer constituting the liposomes. Vesicle-forming lipid includes, but not limited to, phospholipids such as phosphatidylcholine (PC), phosphatidylglycerol (PG), phosphatidylinositol (PI), phosphatidic acid (PA), phosphatidylethanolamine (PE) or phosphatidylserine (PS), and charged lipids, such as a positively charge lipid or a negatively charged lipid.

The lipid bilayer of the liposome includes at least one vesicle-forming lipid and 0 (zero) to less than 15 mole % of sterol (e.g., 0-14.99 mole %), said sterol is selected from the group consisting of cholesterol, cholesteryl hemisuccinate, ergosterol, lanosterol, and any combination thereof, but is not limited thereto. In an exemplary embodiment, the sterol is cholesterol.

In some embodiments, the vesicle-forming lipid is a mixture of a first phospholipid and a second phospholipid. In certain embodiments, the first phospholipid is phosphatidylcholine (PC), which is selected from the group consisting of hydrogenated egg phosphatidylcholine (HEPC), hydrogenated soy phosphatidylcholine (HSPC), dipalmitoyl phosphatidylcholine (DPPC), distearoyl phosphatidylcholine (DSPC), diarachidoyl phosphatidylcholine, dimyristoyl phosphatidylcholine (DMPC), egg phosphatidylcholine (EPC), soy phosphatidylcholine (SPC), oleoyl palmitoyl phosphatidylcholine, dioleoyl phosphatidylcholine (DOPC), dipetroselinoyl phosphatidylcholine, palmitoylelaidoyl phosphatidylcholine, palmitoyloleoyl phosphatidylcholine, dilauroyl phosphatidylcholine (DLPC), diundecanoyl phosphatidylcholine, didecanoyl phosphatidylcholine, dinonanoyl phosphatidylcholine, and any combination thereof. In other embodiments, the second phospholipid is a polyethylene glycol modified phospholipid, containing a polyethylene glycol having a molecular weight of about 500 to about 10,000 daltons, such as 1,2-distearoyl-sn-glycero-3-phosphoethanolamine-N-[methoxy (polyethylene glycol)-2000] (DSPE-PEG2000), a negatively charged phospholipid, such as distearoyl phosphatidylglycerol (DSPG), Dipalmitoylphosphatidylglycerol (DPPG) or dimyristoylphosphatidylglycerol (DMPG) or dioleoyl phosphatidylglycerol (DOPG). In an exemplary embodiment, the mole percent of the first phospholipid:cholesterol:the second phospholipid is 75-99:0-14.9:0.1-25.

In other embodiments, the vesicle-forming lipids are a mixture of a first phospholipid and a charged lipid. In an exemplary embodiment, vesicle-forming lipids are a mixture of a first phospholipid, a second phospholipid and a charged lipid. The charged lipid, includes stearylamine, 1,2-dioleoyl-3-trimethylammonium-propane (DOTAP), 3ß-[N—(N',N'-dimethylaminoethane)-carbamoyl]cholesterol (DC-Cholesterol), $N^4$-Cholesteryl-Spermine (GL67), dimethyldioctadecylammonium (DDAB), 1,2-di-O-octadecenyl-3-trimethylammonium propane (DOTMA), ethylphosphocholine (ethyl PC) or combination thereof. In another exemplary embodiment, the mole percent of the first phospholipid:cholesterol:charged lipid is 75-99:0-14.9:0.1-25.

In an embodiment, the mole % of HSPC, cholesterol, and DSPG in the lipid bilayer is 75-99:0-14.9:0.1-25. In another embodiment, the mole % of HSPC, cholesterol and DSPE-PEG2000 in the lipid bilayer is 75-99:0-14.9:0.1-25.

In one embodiment, the external lipid bilayer of the liposomes further comprises a surfactant, which can be a non-ionic surfactant, a cationic surfactant or a zwitterionic surfactant. A non-ionic surfactant has no formally charged groups in its head. A cationic surfactant carries a net positive charge in its head. A zwitterion surfactant is electrically neutral but carries formal positive and negative charges on different atoms.

Non-limiting examples of non-ionic surfactant include non-ionic water soluble mono-, di-, and tri-glycerides; non-ionic water soluble mono- and di-fatty acid esters of polyethyelene glycol; non-ionic water soluble sorbitan fatty acid esters (e.g. sorbitan monooleates such as TWEEN 20 (polyoxyethylene 20 sorbitan monooleate), SPAN 80); non-ionic water soluble triblock copolymers (e.g., poly(ethyleneoxide)/poly-(propyleneoxide)/poly(ethyleneoxide) triblock copolymers such as POLOXAMER 406 (PLURONIC F-127), or derivatives thereof.

Non-limiting examples of cationic surfactant include dimethyldialkylammonium bromide or dodecyltrimethylammonium bromide.

Non-limiting examples of zwitterionic surfactant include 3-(N,N-dimethyl palmitylammonio)-propanesulfonate.

According to the present invention, the liposomes are prepared in a medium containing a weak acid salt to provide a pH gradient between the internal aqueous medium and the external medium of the liposome. When the vesicle-forming phospholipid and less than 15% of sterol are in contact with a medium containing the weak acid salt, a liposome suspension is formed.

The liposome in the suspension is subjected to size reduction. A liposome's size is typically referred to its diameter. Liposome size reduction can be accomplished by a number of methods, such as extrusion, sonication, homogenization techniques or milling techniques, which are well known and can be performed by persons skilled in this art. Extrusion includes passing liposomes, under pressure, one or more times through filters having defined pore sizes. The filters are generally made of polycarbonate, but can also be made of any durable material which does not interact with the liposomes and which is sufficiently strong to allow extrusion under sufficient pressure. The size of the liposomes can be reduced by sonication, which employs sonic energy to disrupt or shear liposomes that will spontaneously reform into smaller liposomes. For example, sonication can be conducted by immersing a glass tube containing the liposome suspension into the sonic epicenter produced in a bath-type sonicator, or a probe type sonicator may be used in which the sonic energy is generated by vibration of a titanium probe in direct contact with the liposome suspension. In the present invention, the liposomes generally have a diameter of about 50 nm to 500 nm, such as about 500 nm or less, about 400 nm or less, about 300 nm or less, about 200 nm or less or about 100 nm or less.

After sizing, the concentration of the weak acid salt in the external medium is adjusted to provide a pH gradient between the internal aqueous medium and the external medium, which can be carried out by a number of ways, for example, by exchanging the external medium with a suitable buffer lacking the weak acid salts such as citric acid buffer ($H_3C_6H_5O$) and phosphoric acid buffer ($H_3PO_4$), by methods such as diafiltration, dialysis, ultrafiltration, or tangential flow filtration.

The weak acid salt provides a lower outside and a higher inside pH gradient between the external medium and the internal aqueous medium of the liposomes. In one embodiment, the pH of the internal aqueous medium is at least 0.1 unit higher than the pH of the external medium. In another embodiment, the pH of the internal aqueous medium is at least 1 unit higher than the pH of the external medium. In yet another embodiment, the pH of the internal aqueous medium is about 7, 8, 9 or 10 and the pH of the external medium is less than 7, less than 6, less than 5, less than 4, less than 3, about 3-7, about 3.5-6.5, or about 4-6. In yet another exemplary embodiment, the pH of the external medium is above the pKa of the weak acid drug.

Non-limiting examples of weak acid salt include carboxylic acid salt and bicarbonate salt.

"Bicarbonate salt" as used herein refers to a pharmaceutically acceptable salt compound including a bicarbonate anion and a cationic component. In one embodiment, the cationic component of the salt compound is a metal. Non-limiting examples of the metal include a Group IA or IIA metal, such as potassium (K), sodium (Na), calcium (Ca), magnesium (Mg), cesium (Cs), and lithium (Li) or a metal other than Group IA or IIA metal, such as ferrous iron (Fe) and nickel (Ni). Examples of bicarbonate salt include, but not limited to, potassium bicarbonate, sodium bicarbonate, calcium bicarbonate, magnesium bicarbonate, cesium bicarbonate, lithium bicarbonate, nickel bicarbonate, ferrous iron bicarbonate or any combination thereof.

"Carboxylic acid salt" as used herein includes, but not limited to, formate, acetate, propionate, butyrate, isobutyrate, valerate, isovalerate or a combination thereof. In one exemplary embodiment, the acetate is sodium acetate, calcium acetate, or a combination thereof.

The concentration of the bicarbonate salt or carboxylic acid salt is 50 mM or above, 100 mM or above, 150 mM or above, 200 mM or above, 250 mM or above, 300 mM or above, 350 mM or above, 400 mM or above, 450 mM or above, 500 mM or above, 600 mM or above, 700 M or above, 800 mM or above 900 mM, less than 1000 mM, from 50 mM to less than 1000 mM, from 50 mM to 800 mM, from 200 mM to less than 1000 mM, from 200 mM to 800 mM, or from 200 mM to 600 mM, from 250 mM to less than 1000 mM, from 250 mM to 800 mM, or from 250 mM to 600 mM, from 300 mM to 600 mM.

The prepared liposome can be stored for substantial periods of time prior to weak acid drug loading and administration to a subject. For example, liposomes can be stored at refrigerated conditions for substantial periods of time prior to weak acid drug loading. Alternatively, liposomes can be dehydrated, stored, and subsequently rehydrated and loaded with a weak acid drug prior to administration. Liposomes may also be dehydrated after being loaded with the weak acid drug. Dehydration can be performed by a number of methods available and known in the art. In some embodiments, liposomes are dehydrated using standard freeze-drying apparatus i.e. dehydration under low pressure conditions. Also, liposomes can be frozen e.g. using liquid nitrogen. Saccharides can be added to the liposomal environment, e.g., to the buffer containing the liposomes, prior to dehydration, to ensure stability and integrity of the liposome during dehydration. Examples of saccharides include but are not limited to maltose, lactose, sucrose, trehalose, dextrose, sorbitol, mannitol, xylitol, or a combination thereof.

A liposome suspension with less than 15 mole % of sterol or substantially free of sterol as described above are ready for weak acid drug loading. Typically, the weak acid drug is added to the external medium of the liposome and the resultant suspension is incubated, allowing diffusion of the weak acid drug into the internal aqueous medium of the liposome and until a desired loading concentration and encapsulation efficiency (the percentage of the internal/encapsulated amount of the weak acid drug relative to the total amount of the weak acid drug in the pharmaceutical composition composition) is achieved.

B. Association Between Sterol Content in the External Lipid Bilayer and Controlled Release Profile The pharmaceutical composition of the present invention having less than 15 mole percent (e.g., 0-14.99 mole %) of sterol in the liposomal external lipid bilayer reduces the burst release of the encapsulated weak acid drug and hence reduces the side effect of the weak acid drug. Furthermore, sufficient amount of the weak acid drug for a desired therapeutic effect is released from the pharmaceutical composition and the release profile is unexpectedly extended compared to that of the pharmaceutical composition with more than 15 mole percent of sterol in the liposomal external lipid bilayer.

As used herein, the term "burst release" refers to rapid and/or somewhat uncontrolled release of more than 70, 69, 68, 67, 66 or 65% of the encapsulated weak acid drug from the pharmaceutical composition within 1 hour (60 minutes) of administration of the pharmaceutical composition.

As used herein, the term "extended release" can be used interchangeably with "controlled release", "delayed release", "modified release", "prolonged release", "programmed release", "time release", "rate controlled" or "sustained release". and refers to the release of less than 50, 45 or 40% of the weak acid drug within 1 hour after the administration of the pharmaceutical composition.

In one embodiment, the burst release or the sustained release profile of the pharmaceutical composition is based on the in vitro release (IVR) assay and/or the in vivo pharmacokinetics study of entrapped weak acid drug.

In certain embodiments, based on in vitro release (IVR) assay and/or the in vivo pharmacokinetics study, the pharmaceutical composition has a release profile wherein less than about 70, 69, 68, 67, 66 or 65% by weight of the entrapped weak acid drug is released within 1 hour from the time of the pharmaceutical composition administration.

C. Administration

The pharmaceutical composition of the present invention may be administered into a cavity of a subject that does not have a direct contact with the bloodstream. Examples of the routes of administration include, but are not limited to, inhalation, intratracheal injection, subcutaneous injection, intraarticular injection, intramuscular injection, intravitreal injection and intrathecal injection.

The pharmaceutical composition of the present invention may also be administered directly into the bloodstream of a subject.

According to this disclosure, the pharmaceutical composition may be administrated once to three times a day, once every 2 days or once every 3 days.

The present disclosure will be further described in the following examples. However, it should be understood that the following examples are solely intended for the purpose of illustration and should not be construed as limiting the present disclosure in practice.

EXAMPLES

General Experimental Procedures:

1. Preparation of Iloprost Liposomal Composition

A liposomal colloidal suspension was prepared using ethanol injection technique. All of the lipid ingredients, including a first phospholipid (HSPC) and a second phospholipid (DSPE-PEG2000 or DSPG) at a molar ratio of 98:2 or 98.5:1.5 were dissolved in 2.86 mL of ethanol solution at approximately 60° C. The resultant lipid solution was injected into 17.4 mL of sodium bicarbonate solution (100 to 400 mM; pH 8.5) and optionally with (2-Hydroxypropyl)-β-cyclodextrin (i.e., 45 to 120 mM), and mixed under vigorous stirring at 60° C. for liposome hydration. The mixture was extruded 6 to 10 times through polycarbonate membranes with pore size of 0.2 or 0.1 μm to obtain a suspension of liposomes having a mean particle size within a range of around 100 nm to 200 nm and a polydispersity index (PdI) of <0.2. The suspension of liposomes was dialyzed with a tangential flow filtration system against 10 mM of sodium citrate buffer (pH 5.5) to form a transmembrane pH gradient between the internal aqueous medium of the liposome and the external medium (i.e., a higher inside and a lower outside pH gradient). The suspension of liposomes having such pH gradient was then stored at 4° C. before drug loading process.

Iloprost (purchased from Cayman Chemical, USA) was dissolved in 50 mM of sodium citrate solution and added into the suspension of liposomes to achieve a drug concentration from 1000 to 250 μg/mL and incubated at 37° C. for 30 min. The resultant product was adjusted with a sodium citrate buffer (pH 5.5) to obtain an iloprost-loaded liposomal composition having a pH 5.5 in the external medium and a phospholipid concentration of 10 mM in the liposome suspension.

2. Preparation of Ambrisentan Liposomal Composition

A liposome suspension was prepared according to step 1 above with or without the use of (2-Hydroxypropyl)-β-cyclodextrin. Ambrisentan (purchased from Cayman Chemical, USA) was dissolved in dimethyl sulfoxide (DMSO), then added into the suspension of liposomes to achieve a given drug concentration around 500 μg/mL and incubated at 37° C. for 30 min. The resultant product was adjusted with a sodium citrate buffer (pH 5.5) to obtain an ambrisentan-loaded liposomal composition having a pH of 5.5 in the external medium and a phospholipid concentration of 10 mM in the liposome suspension.

3. Quantitative Characterization of Liposomal Compositions a. Concentrations of Encapsulated and Free Iloprost/Ambrisentan:

The iloprost- or ambrisentan-liposomal composition was poured into a PD MiniTrap™ G-25 column (GE Healthcare) to separate encapsulated drug from free drug. The iloprost- or ambrisentan-liposomal composition was mixed with methanol (90 volume % methanol and 10 volume % liposome suspension) to form a liposomal-methanol mixture.

The concentrations of the encapsulated iloprost and the free iloprost were analyzed by injecting 30 μL of the liposomal-methanol mixture into a Waters Acquity HPLC system equipped with a photodiode array (PDA) detector. The mobile phase was a mixture of acetonitrile, methanol and phosphate buffer (pH 2.5) at volume ratio of 36:17:47, and the flow rate of the mobile phase is 1.0 mL/min. Separation was performed using C8 Column, having a dimension of 3.9 mm×15.0 cm, 5.0 μm, at 25° C. and absorbance peak was detected at 205 nm.

The concentrations of the encapsulated ambrisentan and the concentration of free ambrisentan were analyzed by injecting 1 μL of the liposomal-methanol mixture into a Waters Acquity UPLC system equipped with a mass detector (QDa). Mobile phase A included 0.1% formic acid in acetonitrile, and mobile B included 0.1% formic acid in ddH2O. Gradient conditions were as follows: 50% mobile phase A for 0.2 minutes, 10% mobile phase A to 2 minutes, and 50% mobile phase A to 5.5 minutes. Separation was performed using C18 Column, having a dimension of 4.6 mm×10.0 cm, 3.0 μm, at 35° C. with a flow rate of 1.0 mL/min. The MS acquisition was performed with SIR mode using the $[M+H]^+$ ions, m/z 347.2 for ambrisentan.

b. Encapsulation Efficiency (EE) and Drug-to-Cyclodextrin Ratio:

The concentration of total amount of drug (iloprost or ambrisentan) in the liposomal composition includes the encapsulated drug in internal aqueous medium (L) and the free drug in the external medium (F).

Encapsulation efficiency (EE) of the drug was calculated as the percentage of the encapsulated drug in the internal aqueous medium of the liposome (L) relative to the total amount of the drug (L+F), see formula below:

$$EE\ (\%) = [L/(L+F)] \times 100$$

ILO/CD ratio of the iloprost liposomal composition and AMB/CD ratio of the ambrisentan liposomal composition were calculated using the following formulae:

$$ILO/CD \text{ ratio} = \{[ILO] \times EE\}/[CD]$$

$$AMB/CD \text{ ratio} = \{[AMB] \times EE\}/[CD]$$

[ILO] (mM)=the concentration of the total amount of iloprost (L+F)

[AMB] (mM)=the concentration of the total amount of ambristentan (L+F)

EE (%)=the encapsulation efficiency

[CD] (mM)=the cyclodextrin concentration c. Mean Particle Size and Polydispersity Index (PdI):

The mean particle size of the liposome was evaluated by dynamic light scattering. The polydispersity index (PdI), a value indicating the size distribution of the liposomes, was determined using the same evaluation technique as for the mean particle size, using Beckman Coulter Delsa™ Nano C particle analyzer.

Example 1: In Vitro Release (IVR) Profile of Iloprost Liposomal Compositions with Different Amount of Sterol A. In Vitro Release (IVR) Assay The iloprost liposomal compositions were formulated and the concentration of iloprost was analyzed according to the procedures in the preceding General Experimental Procedures sections. The mean particle size of the liposome was 100-200 nm and the PdI was less than 0.20.

Various IVR assays can be used to assess the IVR profile. The actual IVR assay is known, or will be apparent, to those skilled in the art depending on the iloprost in the claimed liposomal composition. The iloprost release profiles from liposome were obtained by a ten-fold dilution for iloprost-loaded liposome solution with a starting phospholipid concentration of 10 mM against simulated lung fluid (SLF) [*Dissolution Technologies* 2011, 18, 15-28] at 37° C. with 100 rpm shaking speed. The percentage of iloprost released (Release %) at each time point was calculated by comparing the encapsulation efficiency (EE) after incubation at specific time point (T) to the initial (To) encapsulation efficiency using the following formula:

$$\text{Release}_{at\ T}\ (\%) = (EE_{at\ T0} - EE_{at\ T})/EE\ \text{at}_{T0}$$

Results:

The physicochemical characterization and IVR profile of iloprost liposomal compositions with different amount of sterol are shown in Table 2.

TABLE 2

| Iloprost Lipid composition (molar ratio) | Liposome internal salt | [ILO] (μg/mL) | EE (%) | PS (nm) | $\text{Release}_{1\ hr}$ (%) |
|---|---|---|---|---|---|
| HSPC/Cholesterol/DSPE-mPEG = 59.1/39.4/1.5 | Bicarbonate 400 mM | 493 | 93.0 | 152.5 | 90.6 |
| HSPC/Cholesterol/ DSPG = 59.1/39.4/1.5 | | 484 | 92.6 | 150.4 | 82.6 |
| HSPC/Cholesterol/DSPE-mPEG = 78.5/20/1.5 | | 477 | 95.3 | 147.3 | 87.8 |
| HSPC/Cholesterol/ DSPG = 78.5/20/1.5 | | 482 | 94.4 | 147.8 | 83.2 |
| HSPC/Cholesterol/DSPE-mPEG = 83.5/15/1.5 | | 490 | 95.3 | 150.2 | 75.3 |
| HSPC/Cholesterol/ DSPG = 83.5/15/1.5 | | 483 | 94.7 | 149.2 | 70.6 |
| HSPC/Cholesterol/DSPE-mPEG = 88.5/10/1.5 | | 486 | 93.6 | 146.7 | 63.2 |
| HSPC/Cholesterol/ DSPG = 88.5/10/1.5 | | 495 | 94.2 | 151.5 | 64.5 |
| HSPC/DSPE-mPEG = 98/2 | | 478 | 97.5 | 161.3 | 52.8 |
| HSPC/DSPG = 98.5/1.5 | | 487 | 94.2 | 156.7 | 57.5 |

Table 2 shows >90% EE was achieved with a sodium bicarbonate salt and iloprost liposomal compositions with less than 15 mole % of cholesterol released less than 65% of the iloprost within 1 hour from the time of SLF incubation, whereas iloprost liposomal compositions with equal to or more than 15 mole % of cholesterol released more than 70% of the iloprost within 1 hour from the time of SLF incubation at 37° C.

Example 2: In Vitro Release (IVR) Profile of Ambrisentan Liposomal Compositions with Different Amount of Sterol The ambrisentan liposomal compositions were formulated and the concentration of ambrisentan was analyzed according to the procedures in the preceding General Experimental Procedures sections. The mean particle size of the liposome was 100-200 nm and the PdI was less than 0.20.

Results:

The physicochemical characterization and IVR profile of ambrisentan liposomal compositions with different amount of sterol are shown in Table 3.

TABLE 2

| Ambrisentan Lipid composition (molar ratio) | Liposome internal salt | [AMB] (μg/mL) | EE (%) | PS (nm) | $\text{Release}_{1hr}$ (%) |
|---|---|---|---|---|---|
| HSPC/Cholesterol/ DSPG = 59.1/39.4/1.5 | Bicarbonate 400 mM | 496 | 96.6 | 151.4 | 95.8 |
| HSPC/Cholesterol/ DSPG = 88.5/20/1.5 | | 493 | 96.4 | 148.5 | 65.7 |
| HSPC/Cholesterol/ DSPG = 88.5/15/1.5 | | 487 | 96.8 | 152.0 | 46.4 |
| HSPC/Cholesterol/ DSPG = 88.5/10/1.5 | | 497 | 97.1 | 145.3 | 32.2 |
| HSPC/ DSPG = 98.5/1.5 | | 484 | 97.1 | 153.4 | 11.9 |

Table 3 shows >95% EE was achieved with a sodium bicarbonate salt and ambrisentan liposomal compositions with less than 15 mole % of cholesterol released less than 50% of the ambrisentan within 1 hour from the time of SLF incubation at 37° C.

Example 3: In Vitro Release (IVR) Profile of Iloprost Liposomal Compositions with or without Cyclodextrin (CD)

An in vitro study was performed to evaluate the effect of cyclodextrin ((2-Hydroxypropyl)-β-cyclodextrin (HP-β-CD)) in the internal aqueous medium of the liposome on the release profile of iloprost liposomal compositions in Example 1.

Results:

The physicochemical characterization and IVR profile of iloprost liposomal compositions with or without cyclodextrin (HP-β-CD) are shown in Table 4.

TABLE 4

| Lipid composition (molar ratio) | Composition of internal aqueous medium | | [ILO] (μg/mL) | EE (%) | PS (nm) | $Release_{1hr}$ (%) |
|---|---|---|---|---|---|---|
| HSPC/DSPE-mPEG = 98/2 | Bicarbonate 400 mM | — | 478 | 97.5 | 161.3 | 52.8 |
| | | HP-β-CD 90 mM | 479 | 98.3 | 161.6 | 31.5 |
| HSPC/DSPG = 98.5/1.5 | | — | 485 | 94.2 | 156.7 | 57.5 |
| | | HP-β-CD 90 mM | 487 | 94.6 | 157.8 | 37.8 |

Table 4 shows the addition of cyclodextrin further reduces burst release (less than 60% of the iloprost was released within 1 hours from the time of SLF incubation at 37° C.) and sustains the release attribute of the iloprost liposomal compositions (less than 40% of the iloprost was released within 1 hours from the time of SLF incubation at 37° C.).

Example 4: Encapsulation Efficiency of Iloprost Liposomal Compositions Using Different Weak Acid Salt An in vitro study was carried out to evaluate the effect of different weak acid salts on the encapsulation efficiency of the iloprost liposomal composition in Example 1. Sodium bicarbonate solution (400 mM), and sodium acetate solution were used to load iloprost in this example.

Results:

The encapsulation efficiency of iloprost liposomal compositions using different weak acid salts are shown in Table 5.

TABLE 5

| Lipid composition (molar ratio) | Composition of internal aqueous medium | | [ILO] (μg/mL) | EE (%) | PS (nm) | $Release_{1hr}$ (%) |
|---|---|---|---|---|---|---|
| HSPC/DSPE-mPEG = 98/2 | Acetate 400 mM | — | 483 | 84.2 | 159.2 | 64.2 |
| | | HP-β-CD 90 mM | 494 | 85.8 | 158.8 | 42.9 |
| | Bicarbonate 400 mM | — | 478 | 97.5 | 161.3 | 52.8 |
| | | HP-β-CD 90 mM | 479 | 98.3 | 161.6 | 31.5 |

Table 5 shows >80% EE was achieved with bicarbonate and acetate salts and the presence of a cyclodextrin in the internal aqueous medium further reduces the burst release and sustains the release of iloprost from the liposomal compositions.

Example 5: In Vitro Release (IVR) Profile and In Vivo Pharmacokinetics (PK) Parameter of Iloprost Liposomal Compositions with Different Iloprost-to-Cyclodextrin (ILO/CD) Ratio An in vitro study was carried out to evaluate the effect of different ILO/CD ratio on the IVR profile of iloprost liposomal compositions. The liposomal compositions of this study were prepared and the IVR profiles were analyzed according to the procedures outlined in Example 1. Iloprost solution (20 μg/mL) was prepared by dissolving iloprost in 2 mM solution of tromethamine, adjusted to a pH of approximately 8.4.

B. In Vivo Pharmacokinetics (PK) Study of Iloprost Liposomal Compositions

In this in vivo PK study, 3 male Sprague-Dawley rats (purchased from BioLASCO Taiwan Co., Ltd.) in each group were anaesthetized with isoflurane, and positioned securely on its back to an arched platform in a dorsal position at a 45° to 50° plane using a ribbon hooked around upper incisors. A microspray aerosol tip (Microsprayer, PennCentury, Philadelphia, USA) was inserted to the tracheal bifurcation of each rat, and a test sample (i.e., compositions in Table 6 or iloprost solution) was administered intra-tracheally to each rat at a given dose of 60 μg/kg using a high-pressure syringe that is attached to a microspray aerosol device.

At a predetermined time point (i.e., 5, 30 min, 1.5, 3, 6, 7 and 8 hours post administration), blood sample was collected from each rat into a heparin coated tube and placed on wet ice. The blood sample was then centrifuged at approximately 2500×g for 15 min and at 4±2° C. within 1 hour of collection, to separate the plasma from the blood cells. Approximately 0.1 mL of the plasma sample from each rat was added into a new storage tube and stored at −70±2° C.

To determine the plasma iloprost concentration, 50 μL of the plasma sample was transferred into a well of a 96-wells plate, followed by addition of 150 μL of acetonitrile to each well. The resultant mixture was vortexed for 1 minute to disrupt the binding of plasma proteins to iloprost, followed by centrifugation at 3000 rpm for 5 minutes. The supernatant (150 μL) was mixed with an equal volume of $H_2O$ and analyzed by liquid chromatography-tandem mass spectrometry (LC-MS/MS) to determine the plasma iloprost concentration of the rat.

Figure 2:
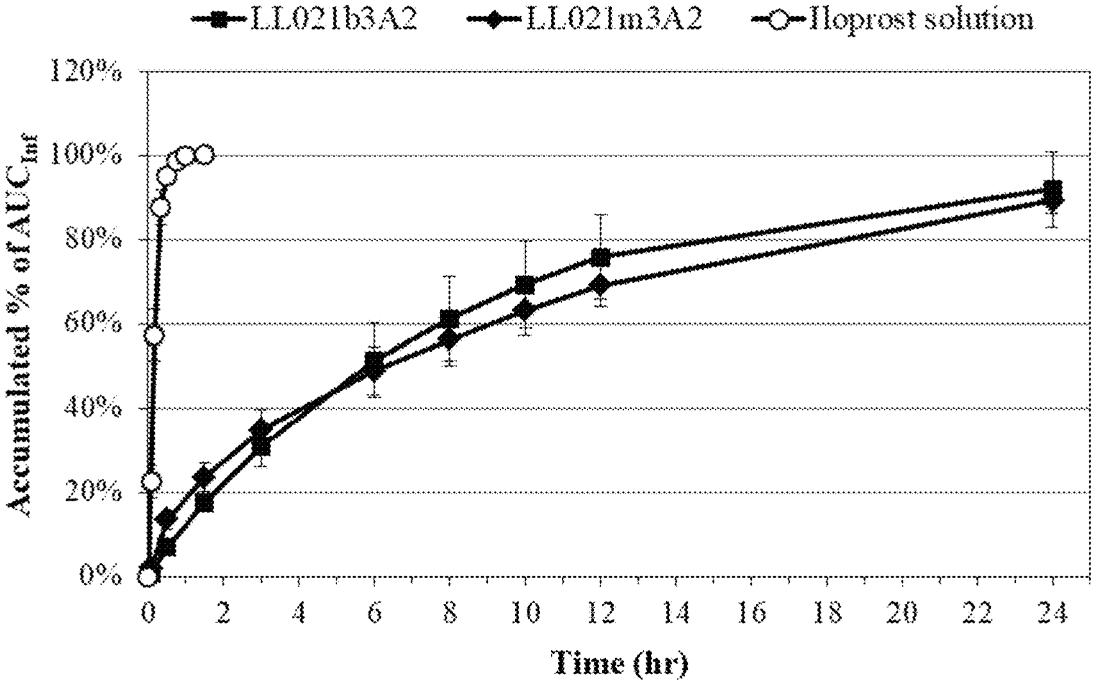
FIG. 2 is a line graph illustrating the ratio of area under the plasma concentration-time curve from time zero to specific time ($AUC_t$) to area under the plasma concentration-time curve from time zero to infinity ($AUC_{inf}$) of a liposomal composition comprising iloprost, bicarbonate and HP-β-CD (LL021b3A2), a liposomal composition comprising iloprost, bicarbonate and RM-β-CD (LL021m3A2), or an iloprost solution.

Results:

The IVR profile and PK parameter ($C_{max}$) of iloprost liposomal compositions with different ILO/CD ratio are shown in Table 6, FIG. 1 and FIG. 2.

TABLE 6

| Formulation[1] | Composition of internal aqueous medium | | [ILO] (μg/mL) | EE (%) | PS (nm) | Release$_{1hr}$ (%) | PK $C_{max}$ (ng/mL) | ILO/CD ratio |
|---|---|---|---|---|---|---|---|---|
| LL023A8 | BCN[2] | — | 988 | 92.1 | 160.7 | 83.6 | — | |
| LL023A5 | 400 mM | | 478 | 97.5 | 161.3 | 52.8 | — | |
| LL023bA8 | | HP-β-CD | 985 | 99.2 | 158.1 | 68.7 | — | 0.0602 |
| LL023bA5 | | 45 mM | 485 | 99.6 | 160.5 | 49.1 | — | 0.0298 |
| LL023b2A8 | | HP-β-CD 90 mM | 920 | 92.0 | 126.5 | 45.0 | 18.25 ± 0.67 | 0.0261 |
| LL021b2A8 | BCN 200 mM | HP-β-CD 90 mM | 920 | 91.0 | 124.8 | 26.4 | 12.88 ± 1.25 | 0.0258 |
| LL022b2A5 | | | 478 | ~100 | 108.1 | 25.8 | 9.93 ± 1.04 | 0.0148 |
| LL021b2A5 | BCN 100 mM | HP-β-CD 90 mM | 473 | 96.4 | 105.7 | 25.7 | 11.07 ± 0.33 | 0.0140 |
| LL021b3A5 | | HP-β-CD 120 mM | 462 | 96.5 | 105.2 | 23.4 | 8.04 ± 1.58 | 0.0103 |
| | | | 507 | 99.0 | 96.6 | 23.3 | 12.33 ± 3.51 | 0.0116 |
| LL021b3A2 | | | 277 | 99.2 | 96.4 | 17.2 | 9.00 ± 2.00 | 0.0063 |
| | | | 259 | 99.6 | 142.7 | 5.6 | 2.33 ± 0.58 | 0.0060 |

[1]The external lipid bilayer comprises 10 mM of lipid (HSPC/DSPE-mPEG = 98:2)
[2]BCN: Bicarbonate Table 6 shows iloprost-liposomal compositions with ILO/CD ratio less than 0.06 display a reduced burst release profile (less than 68.7% of the iloprost is released within 1 hour from the time of administration). A more sustained release attribute (less than 45% of the iloprost is released within 1 hours from the time of SLF incubation at 37° C.) was noted in iloprost-liposomal compositions with ILO/CD ratio less than 0.026. Similar trend was noted with the addition of cyclodextrin in the internal aqueous medium.

FIG. 1 shows the log of plasma mean iloprost concentration in the rats administered with iloprost-liposomal compositions of 7 Table (LL021b3A2/LL021m3A2) or iloprost solution at a given dose versus administration time up to 24 hours. There is no significant peak after the administration of the iloprost-liposomal compositions compared to the peak within 1 hour of administration of the iloprost solution. A reduced peak release prevents the side effect of the drug, for example, less local irritation in the upper respiratory tract upon direct contact with the claimed liposomal composition. administering the iloprost solution. The results show reduced drug accumulation at the target site and hence, less side effect.

Example 6: In Vitro Release (IVR) Profile and In Vivo Pharmacokinetics (PK) Parameter of Iloprost Liposomal Compositions with Different Cyclodextrin (CD)

Iloprost liposomal compositions comprising (2-Hydroxypropyl)-β-cyclodextrin (HP-β-CD) or randomly methylated-β-cyclodextrin (RM-β-CD) were prepared and the IVR profiles were assessed according to the procedures outline in Example 1.

Results:

Table 7 shows the physicochemical characterization of iloprost liposomal compositions with different CDs. Both HP-β-CD and RM-β-CD reduced the burst release of iloprost-liposomal compositions (less than 20% of the iloprost is released within 1 hours from the time of SLF incubation at 37° C.).

TABLE 7

| Formulation[1] | Composition of internal aqueous medium | | [ILO] (μg/mL) | EE (%) | PS (nm) | Release$_{1hr}$ (%) | PK $C_{max}$ (ng/mL) | ILO/CD ratio |
|---|---|---|---|---|---|---|---|---|
| LL021b3A2 | BCN[2] 100 mM | HP-β-CD 120 mM | 259 | 99.6 | 142.7 | 5.6 | 2.33 ± 0.58 | 0.0060 |
| LL021m3A2 | | RM-β-CD 120 mM | 284 | 99.4 | 147.4 | 9.6 | 6.00 ± 1.73 | 0.0066 |

[1]Lipid composition (10 mM of lipid): HSPC/DSPE-mPEG = 98:2.
[2]BCN: Bicarbonate FIG. 2 shows the ratio of area under the plasma concentration-time curve from time zero to specific time (AUC$_t$) to area under the plasma concentration-time curve from time zero to infinity (AUC$_{inf}$) to determine the total exposure of iloprost over a time period and for normalizing different dosage of iloprost in each composition (iloprost-liposomal compositions of Table 7 or iloprost solution). More than 80% of the iloprost was released within 24 hours from the time of administration of the iloprost-liposomal compositions compared to 100% iloprost release within 1 hour of In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment", "an embodiment", an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

What is claimed is:

1. A pharmaceutical composition, comprising:
one or more liposomes suspended in an external medium, said liposome comprises:
(a) an external lipid bilayer, comprising
(i) 75-99 mole % of a phosphatidylcholine,
(ii) 0.1-25 mole % of a phosphatidylglycerol, a phosphoethanolamine, a phosphatidic acid, stearylamine or DDAB and
(iii) less than 15 mole % of a sterol; and
(b) an internal aqueous medium, comprising a weak acid drug and a weak acid salt that is a carboxylic acid salt or bicarbonate salt,
wherein the pharmaceutical composition is incubated with a simulated lung fluid and less than 65% of the weak acid drug is released into the simulated lung fluid within 1 hour of the incubation.

2. The pharmaceutical composition of claim 1, wherein the external medium is citric acid buffer or phosphoric acid buffer.

3. The pharmaceutical composition of claim 1, wherein the external lipid bilayer comprises less than 13 mole % of sterol.

4. The pharmaceutical composition of claim 1, wherein the external lipid bilayer comprises less than 10 mole % of sterol.

5. The pharmaceutical composition of claim 1, wherein the external lipid bilayer is substantially free of sterol.

6. The pharmaceutical composition of claim 1, wherein the sterol is cholesterol, cholesteryl hemisuccinate, ergosterol, lanosterol, or any combination thereof.

7. The pharmaceutical composition of claim 1, wherein said phosphatidylcholine is hydrogenated egg hydrogenated soy phosphatidylcholine, dipalmitoyl phosphatidylcholine, distearoyl phosphatidylcholine, diarachidoyl phosphatidylcholine, dimyristoyl phosphatidylcholine, egg phosphatidylcholine, soy phosphatidylcholine, oleoyl palmitoyl phosphatidylcholine, dioleoyl phosphatidylcholine, dipetroselinoyl phosphatidylcholine, palmitoylelaidoyl phosphatidylcholine, palmitoyloleoyl phosphatidylcholine, dilauroyl phosphatidylcholine, diundecanoyl phosphatidylcholine, didecanoyl phosphatidylcholine, dinonanoyl phosphatidylcholine, or any combination thereof, said phosphoethanolamine is 1,2-distearoyl-sn-glycero-3-phosphoethanolamine-N-[methoxy (polyethylene glycol)-2000], said phosphatidylglycerol is distearoyl phosphatidylglycerol, dipalmitoylphosphatidylglycerol, dimyristoylphosphatidylglycerol or dioleoyl phosphatidylglycerol, said phosphatidic acid is 1,2-Dipalmitoyl-sn-glycero-3-phosphate, sodium salt.

8. The pharmaceutical composition of claim 1, wherein the phosphatidylcholine is hydrogenated egg phosphatidylcholine, egg phosphatidylcholine, dipalmitoyl phosphatidylcholine or distearoyl phosphatidylcholine, the phosphoethanolamine is 1,2-distearoyl-sn-glycero-3-phosphoethanolamine-N-[methoxy (polyethylene glycol)-2000], the phosphatidylglycerol is distearoyl phosphatidylglycerol, Dipalmitoylphosphatidylglycerol, dimyristoylphosphatidylglycerol or dioleoyl phosphatidylglycerol and the sterol is cholesterol.

9. The pharmaceutical composition of claim 1, wherein the carboxylic acid salt is formate, acetate, propionate, butyrate, isobutyrate, valerate, isovalerate, benzoate or any combination thereof.

10. The pharmaceutical composition of claim 1, wherein the bicarbonate salt is potassium bicarbonate, sodium bicarbonate, calcium bicarbonate, magnesium bicarbonate, cesium bicarbonate, lithium bicarbonate, nickel bicarbonate, ferrous iron bicarbonate or any combination thereof.

11. The pharmaceutical composition of claim 1, wherein the internal aqueous medium further comprises cyclodextrin.

12. The pharmaceutical composition of claim 11, wherein the molar ratio of the weak acid drug to cyclodextrin is less than or equal to 0.06.

13. The pharmaceutical composition of claim 1, wherein the weak acid drug is a prostaglandin, a prostacyclin receptor agonist, an endothelin-receptor antagonist, a glucocorticosteroid, or a non-steroidal anti-inflammatory drug.

14. The pharmaceutical composition of claim 13, wherein the prostaglandin is iloprost or treprostinil, the prostacyclin receptor agonist is MRE-269, the endothelin receptor antagonist is ambrisentan or bosentan, the glucocorticosteroid is methylprednisolone or dexamethasone and the non-steroidal anti-inflammatory drug is ketorolac, piroxicam or meloxicam.

15. The pharmaceutical composition of claim 1, wherein the weak acid drug is encapsulated in the internal aqueous medium of the liposome with an encapsulation efficiency over 70%.

16. A pharmaceutical composition, comprising: one or more liposomes suspended in an external medium, said liposomes comprising:
(a) an external lipid bilayer, comprising a mixture of
(i) 75-99 mole % of a phosphatidylcholine,
(ii) 0.1-25 mole % a phosphatidylglycerol, a phosphoethanolamine, a phosphatidic acid, stearylamine or DDAB, and
(iii) less than 13 mole % of a sterol and
(b) an internal aqueous medium, comprising a weak acid drug and a weak acid salt,
wherein the pharmaceutical composition has an in vitro release profile obtained by incubating the pharmaceutical composition with a simulated lung fluid, and less than 65% of the weak acid drug is released into the simulated lung fluid within one hour,
wherein the sterol is cholesterol, cholesteryl hemisuccinate, ergosterol, lanosterol, or a combination thereof;
wherein the weak acid salt is carboxylic acid salt or bicarbonate salt;
wherein the carboxylic acid salt is formate, acetate, propionate, butyrate, isobutyrate, valerate, isovalerate, benzoate or any combination thereof; and
wherein the bicarbonate salt is potassium bicarbonate, sodium bicarbonate, calcium bicarbonate, magnesium bicarbonate, cesium bicarbonate, lithium bicarbonate, nickel bicarbonate, ferrous iron bicarbonate or any combination thereof,
wherein the pH of the external medium is above the pKa of the weak acid drug, and wherein the weak acid drug is a prostaglandin or an endothelin receptor antagonist.

* * * * *